United States Patent
Tamonoki

(10) Patent No.: US 11,375,114 B2
(45) Date of Patent: Jun. 28, 2022

(54) CONTROL DEVICE AND OBSERVATION SYSTEM

(71) Applicant: Sony Olympus Medical Solutions Inc., Tokyo (JP)

(72) Inventor: Sadayuki Tamonoki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 43 days.

(21) Appl. No.: 16/662,058

(22) Filed: Oct. 24, 2019

(65) Prior Publication Data
US 2020/0137345 A1  Apr. 30, 2020

(30) Foreign Application Priority Data

Oct. 31, 2018  (JP) .............................. JP2018-205988

(51) Int. Cl.
*H04N 5/232* (2006.01)
*H04N 5/225* (2006.01)
(Continued)

(52) U.S. Cl.
CPC ....... *H04N 5/23245* (2013.01); *A61B 1/0002* (2013.01); *A61B 1/00006* (2013.01); *A61B 1/00039* (2013.01); *A61B 1/00045* (2013.01); *A61B 1/00188* (2013.01); *H04N 1/212* (2013.01); *H04N 1/2141* (2013.01); *H04N 5/2254* (2013.01); *H04N 5/23212* (2013.01); *H04N 5/232935* (2018.08);
(Continued)

(58) Field of Classification Search
CPC ............... H04N 1/212; H04N 5/23245; H04N 5/23293; H04N 5/232933; H04N 5/232935; H04N 7/183; H04N 7/185; H04N 7/186; H04N 1/00129; H04N 5/23206; H04N 5/23209; H04N 2005/2255

See application file for complete search history.

(56) References Cited

U.S. PATENT DOCUMENTS

| 2002/0033882 A1* | 3/2002 | Wada | H04N 7/183 348/65 |
| 2006/0119711 A1* | 6/2006 | Ejima | H04N 1/215 348/222.1 |

(Continued)

FOREIGN PATENT DOCUMENTS

WO   2012/160634 A1   11/2012

*Primary Examiner* — Paul M Berardesca
(74) *Attorney, Agent, or Firm* — Xsensus LLP

(57) ABSTRACT

A control device includes a processor configured to: perform movie display control of causing a display to sequentially display images acquired in time series, and still image display control of causing the display to display any of the images as a still image; detect a first operation on a switch; determine whether a predetermined operation condition for the switch is satisfied, after the first operation has been detected; switch, when the first operation is detected while the movie display control is being executed, from the movie display control to the still image display control and causing the display to display, as a still image, an image displayed at a timing at which the first operation is detected; and cause, when the processor determines that the predetermined operation condition is satisfied, a memory to store the image displayed as a still image under the still image display control.

8 Claims, 13 Drawing Sheets

(51) Int. Cl.
*A61B 1/00* (2006.01)
*H04N 1/21* (2006.01)
*H04N 5/765* (2006.01)
*H04N 101/00* (2006.01)

(52) U.S. Cl.
CPC ..... *H04N 5/765* (2013.01); *H04N 2005/2255* (2013.01); *H04N 2101/00* (2013.01); *H04N 2201/0079* (2013.01)

(56) References Cited

U.S. PATENT DOCUMENTS

| | | | |
|---|---|---|---|
| 2016/0295086 A1* | 10/2016 | Bhat | G06T 7/0012 |
| 2017/0034484 A1* | 2/2017 | Yanagidate | H04N 7/185 |
| 2018/0177382 A1* | 6/2018 | Yagi | H04N 5/232935 |
| 2018/0288361 A1* | 10/2018 | Hirano | H04N 5/23209 |
| 2021/0076903 A1* | 3/2021 | Urasaki | A61B 1/00043 |

\* cited by examiner

CONTROL DEVICE AND OBSERVATION SYSTEM

The present application claims priority to and incorporates by reference the entire contents of Japanese Patent Application No. 2018-205988 filed in Japan on Oct. 31, 2018.

BACKGROUND

The present disclosure relates to a control device and an observation system.

In medical and industrial fields, an observation system for observing the inside of a subject such as a person or a mechanical structure has been known (see, for example, WO 2012/160634).

The observation system (endoscope apparatus) described in WO 2012/160634 includes an endoscope that is inserted into a subject, captures images of the inside of the subject, and outputs an image signal, a control device (control unit) that processes the image signal to generate a video signal for displaying, and a display device (monitor) that displays an image based on the video signal.

In the observation system described in WO 2012/160634, the endoscope is provided with a switch that receives a user operation. With this single switch, the observation system is configured to be capable of executing a plurality of functions.

For example, the user checks images captured by the endoscope in time series and sequentially displayed (movie display) on the display device, and short presses the switch (presses the switch for only a short period of time) when he or she wants to temporarily stop the image sequence (to display a still image). Upon determining that the switch has been short pressed, the control device executes image freeze processing.

On the other hand, the user checks images captured by the endoscope in time series and displayed on the display device as a movie, and long presses the switch (pressed for a longer period of time than in the case of the short pressing) when he or she wants to store an image displayed at a certain timing as a still image. Upon determining that the switch has been long pressed, the control device stores the image as a still image.

SUMMARY

In the observation system described in WO 2012/160634, to store the image displayed on the display device as a still image, the user has to long press the switch while checking the images displayed on the display device as a movie. Thus, the user operates the switch while checking the images displayed as a movie on the display device, and thus may fail to store the desired image, that is, store an image displayed on the display device at a timing different from that of the image, as a still image.

According to one aspect of the present disclosure, there is provided a control device including: a processor including hardware, the processor being configured to: perform movie display control of causing a display to sequentially display a plurality of images acquired in time series, and still image display control of causing the display to display any of the plurality of images as a still image; detect a first operation on a switch by a user; determine whether a predetermined operation condition for the switch is satisfied, after the first operation has been detected; switch, when the first operation is detected while the movie display control is being executed, from the movie display control to the still image display control and causing the display to display, as a still image, an image displayed at a timing at which the first operation is detected; and cause, when the processor determines that the predetermined operation condition is satisfied, a memory to store the image displayed as a still image under the still image display control.

DETAILED DESCRIPTION

Figure 1:
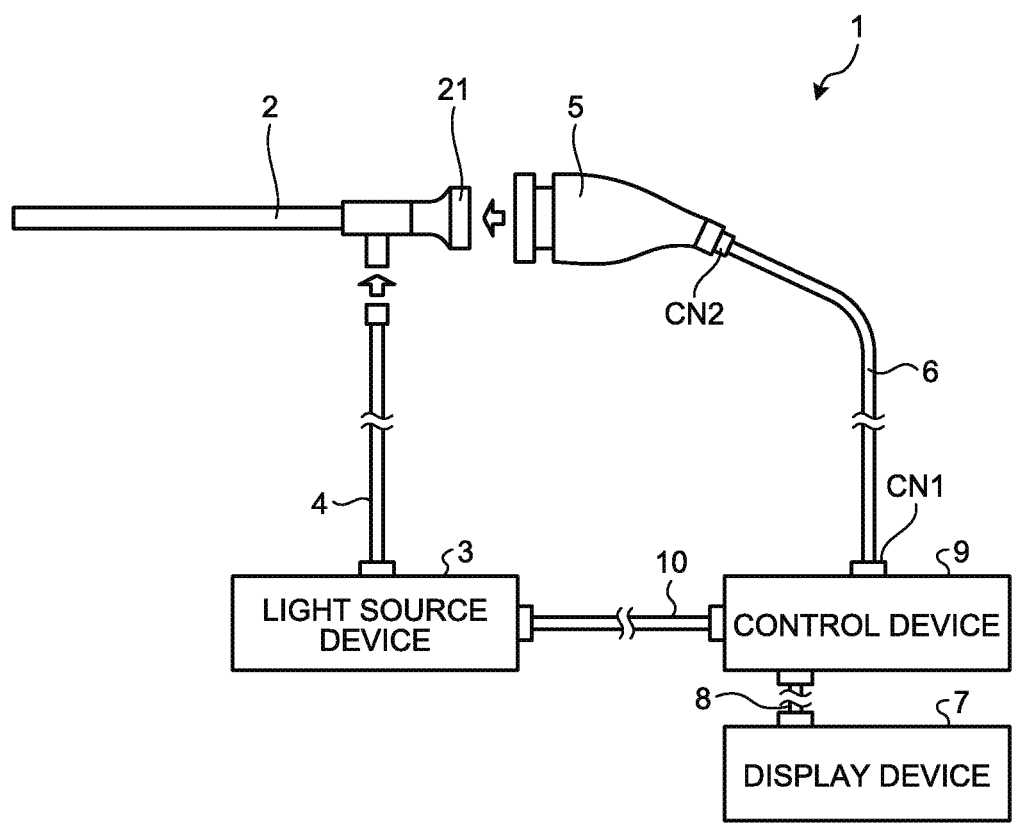
FIG. 1 is a diagram illustrating a configuration of an observation system according to a first embodiment.

Hereinafter, modes for carrying out the present disclosure (hereinafter referred to as embodiments) will be described with reference to the drawings. The present disclosure is not limited to the embodiments described below. Furthermore, in the drawings, the same components are denoted with the same reference numerals.

First Embodiment

Configuration of Observation System

FIG. 1 is a diagram illustrating a configuration of an observation system 1 according to this first embodiment The observation system 1 is a system that is used in the medical field for observing the inside of a subject (in a living body). As illustrated in FIG. 1, the observation system 1 includes an insertion portion 2, a light source device 3, a light guide 4, a camera head 5, a first transmission cable 6, a display device 7, and a second transmission cable 8, a control device 9, and a third transmission cable 10.

In the first embodiment, the insertion portion 2 is formed by a rigid endoscope. Specifically, the insertion portion 2, inserted into a living body, has an elongated shape that is entirely rigid or is partially soft and partially rigid, and is provided with an eyepiece 21 at the proximal end. The insertion portion 2 is provided with an optical system that includes one or a plurality of lenses and focuses light for a subject image.

The light source device 3 is connected to one end of the light guide 4 and supplies light for illuminating the living body to one end of the light guide 4 under the control of the control device 9. In the first embodiment, the light source device 3 is formed to be separated from the control device 9. However, this should not construed in a limiting sense, and a configuration where the light source device 3 is provided inside the control device 9 may be employed.

The light guide 4 has one end detachably connected to the light source device 3, and the other end detachably connected to the insertion portion 2. The light supplied from the light source device 3 travels from one end of the light guide 4 to the other end to be supplied to the insertion portion 2. The light supplied to the insertion portion 2 is emitted onto the living body from the distal end of the insertion portion 2. Light (subject image) emitted into the living body and reflected in the living body is captured by the insertion portion 2.

The camera head 5 is detachably connected to the eyepiece 21 of the insertion portion 2. Then, the camera head 5 captures a subject image that is captured by the insertion portion 2 and emitted from the proximal end of the insertion portion 2, and outputs an image signal (RAW signal) as a result of the image capturing, under the control of the control device 9. The image signal is, for example, an image signal of 4K or of a higher quality.

The detailed configuration of the camera head 5 will be described later.

The first transmission cable 6 has one end detachably connected to the control device 9 via a connector CN1 (FIG. 1) and the other end detachably connected to the camera head 5 via a connector CN2 (FIG. 1). Through the first transmission cable 6 an image signal and the like output from the camera head 5 is transmitted to the control device 9, and a control signal, a synchronization signal, clock, power, and the like, output from the control device 9, are each transmitted to the camera head 5.

Note that the transmission of the image signal or the like from the camera head 5 to the control device 9 through the first transmission cable 6 may be implemented by transmitting the image signal or the like as an optical signal or as an electrical signal. The same applies to transmission of the control signal, the synchronization signals, and the clock transmitted from the control device 9 to the camera head 5 through the first transmission cable 6.

The display device 7 is formed by a display using liquid crystal, organic Electro Luminescence (EL), or the like, and displays an image based on the video signal from the control device 9 under the control of the control device 9.

The second transmission cable 8 has one end detachably connected to the display device 7, and has the other end detachably connected to the control device 9. Through the second transmission cable 8, the video signal, processed by the control device 9, is transmitted to the display device 7.

The control device 9 includes a Central Processing Unit (CPU) and the like, and comprehensively controls the operations of the light source device 3, the camera head 5, and the display device 7.

The detailed configuration of the control device 9 will be described later.

The third transmission cable 10 has one end detachably connected to the light source device 3, and has the other end detachably connected to the control device 9. Through the third transmission cable 10, the control signal, from the control device 9, is transmitted to the light source device 3.

Configuration of Camera Head

Figure 2:
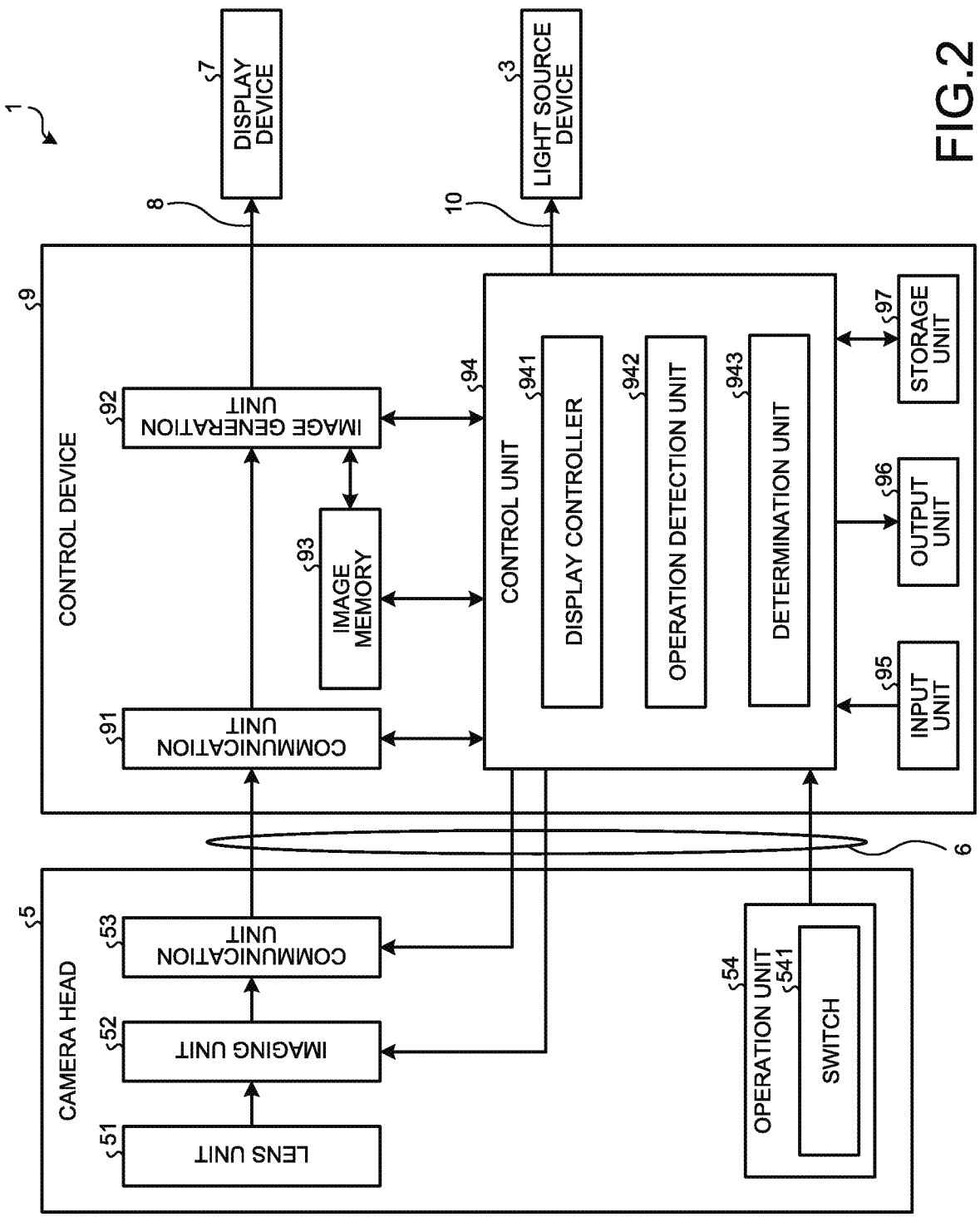
FIG. 2 is a block diagram illustrating configurations of a camera head and a control device.

FIG. 2 is a block diagram illustrating configurations of the camera head 5 and the control device 9.

In FIG. 2, for the sake of description, the connectors CN1 and CN2 between the control device 9 and the camera head 5 and the first transmission cable 6, as well as connectors between the control device 9 and the display device 7 and the second transmission cable 8 and connectors between the control device 9 and the light source device 3 and the third transmission cable 10 are omitted from the drawing.

Next, the configuration of the camera head 5 will be described with reference to FIG. 2.

The camera head 5 includes a lens unit 51, an imaging unit 52, a communication unit 53, and an operating unit 54.

The lens unit 51 forms the subject image, captured by the insertion portion 2, on an image plane of the imaging unit 52.

The imaging unit 52 captures the subject image under the control of the control device 9. Although not elaborated in the figure, the imaging unit 52 includes an image sensor such as a Charge Coupled Device (CCD) or a Complementary Metal Oxide Semiconductor (CMOS) that receives the light corresponding to the subject image formed by the lens unit 51 and converts it into an electrical signal (analog signal), and a signal processing unit that performs signal processing on the electrical signal (analog signal) from the image sensor and outputs an image signal (RAW signal (digital signal)).

The communication unit 53 functions as a transmitter that transmits the image signal (RAW signal (digital signal)), output from the imaging unit 52, to the control device 9 through the first transmission cable 6. For example, the communication unit 53 includes a high-speed serial interface that performs image signal communication with the control device 9 through the first transmission cable 6 at a transmission rate of 1 Gbps or more.

The operating unit 54 is a unit that is exposed to the outside from an exterior housing (not illustrated) of the camera head 5 and receives a user operation by a user such as a doctor. The operating unit 54 includes a switch 541 as illustrated in FIG. 2.

In the first embodiment, the switch 541 is formed by a push button switch. Then, the switch 541 outputs an operation signal corresponding to the pressing (first operation) by a user such as a doctor to the control device 9 through the first transmission cable 6.

Configuration of Control Device

Next, the configuration of the control device 9 will be described with reference to FIG. 2.

The control device 9 includes a communication unit 91, an image generation unit 92, an image memory 93, a control unit 94, an input unit 95, an output unit 96, and a storage unit 97.

The communication unit 91 functions as a receiver that receives the image signal (RAW signal (digital signal)) output from the camera head 5 (communication unit 53) through the first transmission cable 6. For example, the communication unit 91 includes a high-speed serial interface that performs image signal communication with the communication unit 53 at a transmission rate of 1 Gbps or more.

Based on the image signal (RAW signal (digital signal)) output from the camera head 5 and received by the communication unit 91, the image generation unit 92 generates a video signal that is a first video signal or a second video signal, under the control of the control unit 94. Then, the image generation unit 92 transmits the first video signal or the second video signal to the display device 7 through the second transmission cable 8.

Specifically, the image generation unit 92 generates the first video signal in the following manner.

The image generation unit 92 temporarily stores an image signal (RAW signal (digital signal)) output from the camera head 5 and received by the communication unit 91, sequentially in the image memory 93, for each of a predetermined number of frames. Then, the image generation unit 92 sequentially reads out the image signals from the image memory 93, and executes various types of image processing such as development processing, noise reduction, color correction, color enhancement, and edge enhancement on the image signals to generate the first video signal. Then, based on the first video signal, the display device 7 displays images captured in time series by the camera head 5 as a movie.

Specifically, the image generation unit 92 generates the second video signal in the following manner.

The image generation unit 92 stops storing the image signals output from the camera head 5 and received by the communication unit 91, in the image memory 93. Furthermore, the image generation unit 92 reads out an image signal for one frame (hereinafter referred to as a corresponding image signal) designated by the control unit 94 among the image signals for several frames already stored in the image memory 93, and executes various types of image processing such as development processing, noise reduction, color correction, color enhancement, and edge enhancement on the corresponding image signal to generate the second video signal. Then, based on the second video signal, the display device 7 displays an image captured by the camera head 5 as a still image.

The control unit 94 is formed by using, for example, a CPU and the like, and outputs a control signal through the first to third transmission cables 6, 8, and 10, to control the light source device 3, the camera head 5, and the display device 7, and to control overall operations of the control device 9. The control unit 94 includes a display controller 941, an operation detection unit 942, and a determination unit 943.

The display controller 941 is assumed to be capable of executing each of movie display control of controlling an operation of the image generation unit 92 to cause the image generation unit 92 to generate the first video signal and still image display control of controlling an operation of the image generation unit 92 to cause the image generation unit 92 to generate the second video signal.

Here, the movie display control is control for sequentially displaying (movie display) a plurality of images, acquired (captured) in time series by the camera head 5, on the display device 7. The still image display control is control for displaying any one of the plurality of images on the display device 7 (still image display).

Based on the operation signal output from the switch 541, the operation detection unit 942 detects pressing (first operation) of the switch 541 by a user such as a doctor.

The determination unit 943 determines whether a predetermined operation condition for the switch 541 is satisfied after the first operation has been detected by the operation detection unit 942.

In the first embodiment, the determination unit 943 determines that the predetermined operation condition is satisfied when a continued time in which the operation detection unit 942 detects the pressing of the switch 541 (pressing time during which the switch 541 is continuously pressed) reaches a predetermined time. Furthermore, the determination unit 943 determines that the specific operation condition is not satisfied when the pressing of the switch 541 ends before the pressing time reaches the predetermined time.

The input unit 95 is formed by using operation devices such as a mouse, a keyboard, and a touch panel, and receives a user operation by a user such as a doctor. Then, the input unit 95 outputs an operation signal corresponding to the user operation to the control unit 94.

The output unit 96 is formed by using a speaker, a printer, or the like, and outputs various types of information.

The storage unit 97 corresponds to a memory. The storage unit 97 stores a program executed by the control unit 94, information necessary for processing of the control unit 94, a corresponding image signal corresponding to an image displayed as a still image on the display device 7, and the like.

Operation of Control Device

Figure 3:
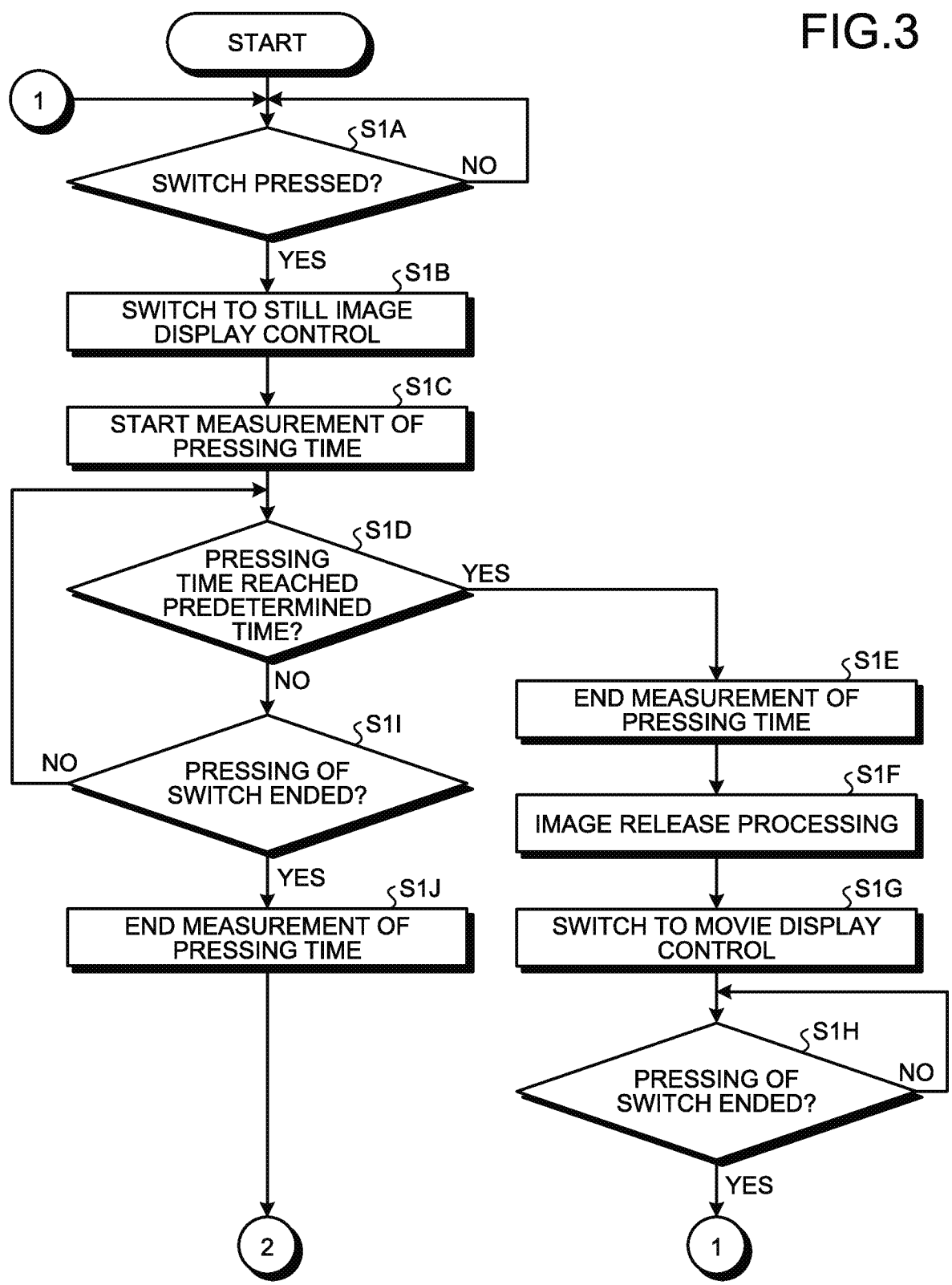
FIG. 3 is a flowchart illustrating an operation of the control device.
Figure 4:
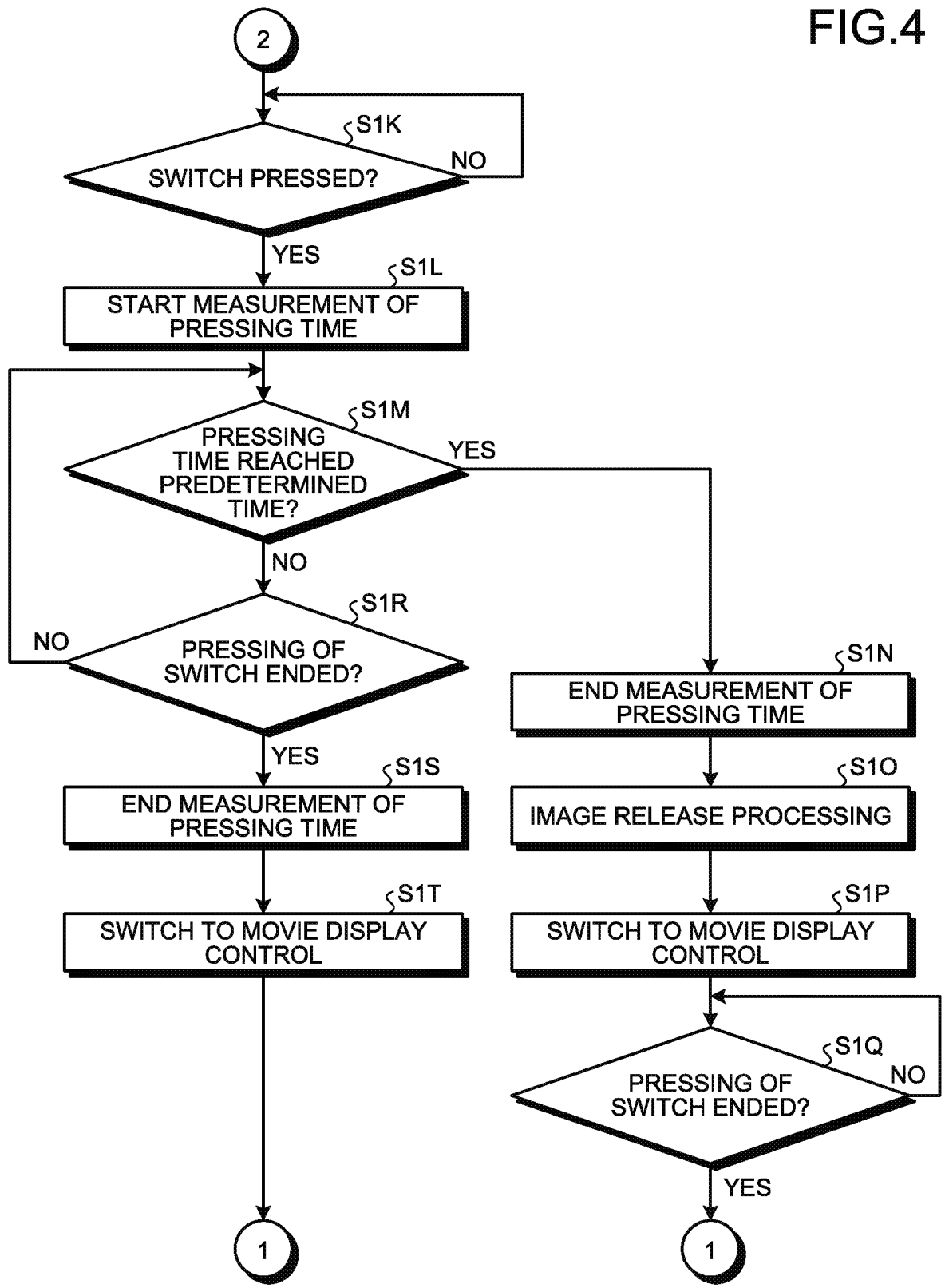
FIG. 4 is a flowchart illustrating an operation of the control device.

FIGS. 3 and 4 are flowcharts illustrating operations of the control device 9. FIGS. 5 to 8 are time charts illustrating the operations of the control device 9. Specifically, (a) in FIGS. 5 to 8 illustrates an operation signal output from the switch 541, which rises to High level when the switch 541 is pressed, and lowers to Low level when the pressing of the switch 541 ends (when the user's hand is released from the switch 541). Note that in (a) in FIGS. 5 to 8, a pressing start timing TS is a timing at which the pressing of the switch 541 starts and a pressing end timing TE is a timing at which the pressing of the switch 541 ends. Further, (b) in FIGS. 5 to 8 illustrates control performed by the display controller 941.

Next, the operations of the control device 9 described above will be described with reference to FIGS. 3 to 8. In the following, for the sake of description, it is assumed that the control device 9 executes the following steps S1A to S1T from the state in which the images captured in time series by the camera head 5 by the movie display control are displayed as movies on the display device 7.

First of all, the operation detection unit 942 constantly monitors whether the switch 541 has been pressed by a user such as a doctor (step S1A).

When the operation detection unit 942 detects pressing of the switch 541 (step S1A: Yes), the display controller 941 identifies the corresponding image signal corresponding to an image displayed on the display device 7 at the pressing start timing TS, in image signals for several frames temporarily stored in the image memory 93. Then, the display controller 941 designates the corresponding image signal for the image generation unit 92, to switch from the movie display control to the still image display control. As a result, the image generation unit 92 stops storing the image signal transmitted from the camera head 5 in the image memory 93, reads out the corresponding image signal from the image memory 93, and performs various types of image processing on the corresponding image signal to generate the second video signal. Then, based on the second video signal, the display device 7 displays an image corresponding to the corresponding image signal as a still image.

As described above, as illustrated in FIG. 5 or 6, the display controller 941 executes the still image display control (image freeze processing) to cause the display device 7 to display the image, displayed at the pressing start timing TS, as a still image (step S1B).

When the operation detection unit 942 detects the pressing of the switch 541 (step S1A: Yes), the determination unit 943 starts measuring the pressing time during which the switch 541 is continuously pressed (Step S1C).

In FIG. 3, for the sake of description, step S1C is executed after step S1B. Actually, however, steps S1B and S1C are executed substantially simultaneously.

After step S1C, the determination unit 943 determines whether the measured pressing time has reached a predetermined time Th (FIGS. 5 and 6) (step S1D).

When it is determined that the pressing time has reached the predetermined time Th (step S1D: Yes), the determination unit 943 ends the measurement of the pressing time (step S1E).

When it is determined that the pressing time has reached the predetermined time Th (step S1D: Yes), the display controller 941 reads the corresponding image signal from the image memory 93 and causes the storage unit 97 to store the corresponding image signal. Thus, the display controller 941 performs so-called image release processing in which the corresponding image signal corresponding to the image displayed on the display device 7 as a still image is stored in the storage unit 97 (step S1F).

In FIG. 3, for the sake of description, step S1F is executed after step S1E. Actually, however, steps S1E and S1F are executed substantially simultaneously.

After step S1F, the display controller 941 switches from the still image display control to the movie display control (step S1G). As a result, the image generation unit 92 resumes the storing of the image signal transmitted from the camera head 5 in the image memory 93, sequentially reads out image signals from the image memory 93, and performs various types of image processing on the image signals to generate the first video signal. Then, based on the first video signal, the display device 7 displays images captured in time series by the camera head 5 as a movie.

After step S1G, the operation detection unit 942 constantly monitors whether the pressing of the switch 541 by the user such as a doctor has ended (step S1H).

When the operation detection unit 942 detects that the pressing of the switch 541 has ended (step S1H: Yes), the control device 9 returns to step S1A.

Figure 5:
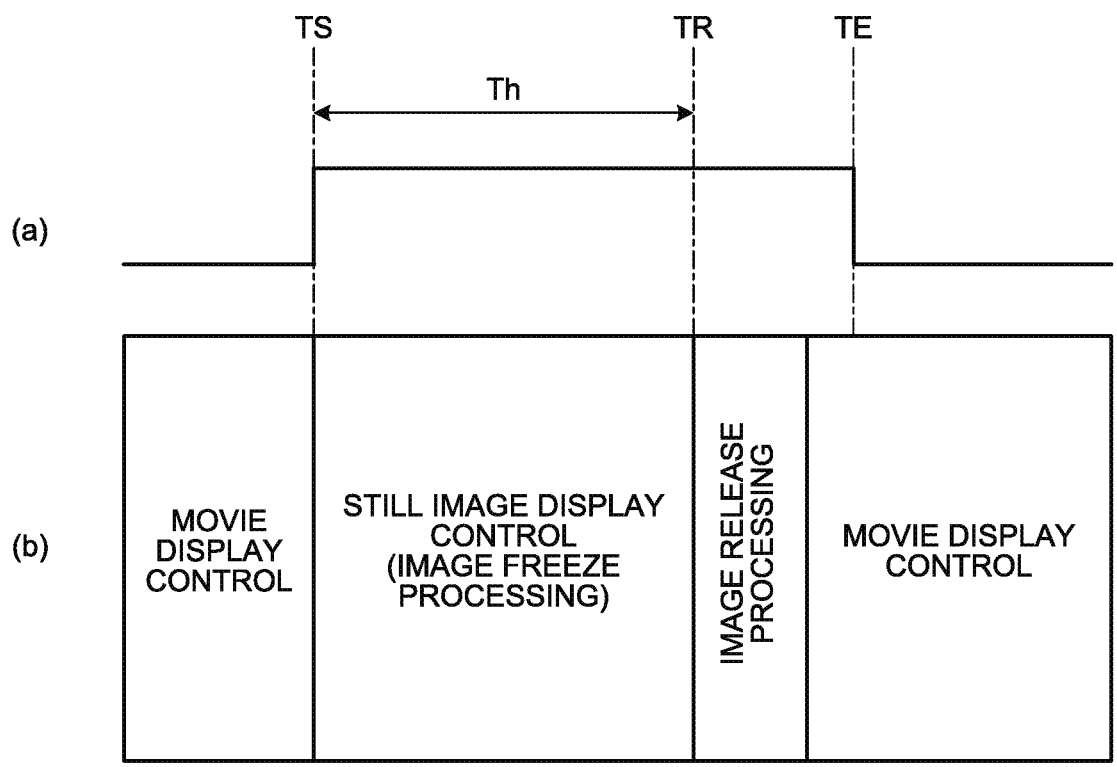
FIG. 5 is a time chart illustrating an operation of the control device.

FIG. 5 is a time chart illustrating the control performed by the display controller 941 in steps S1A to S1H described above when the switch 541 is long pressed (pressed by a time exceeding the predetermined time Th) by the user such as a doctor.

Steps S1A to S1H described above are summarized as follows.

As illustrated in FIG. 5, when the operation detection unit 942 detects that the switch 541 is pressed while the movie display control is being executed (step S1A: Yes), the display controller 941 switches from the movie display control to the still image display control at the pressing start timing TS (step S1B). As a result, the image displayed at the pressing start timing TS is displayed on the display device 7 as a still image. Then, when the determination unit 943 determines that the pressing time has reached the predetermined time Th (step S1D: Yes), the display controller 941 executes the image release processing at a reaching timing TR (FIG. 5) at which the predetermined time Th is reached (step S1F). The timing for executing the image release processing may be the pressing end timing TE as long as it is after the reaching timing TR. Then, the display controller 941 switches from the still image display control to the movie display control (step S1G).

Returning to step S1D, when it is determined that the pressing time has not reached the predetermined time Th (step S1D: No), the operation detection unit 942 determines whether the pressing of the switch 541 by the user such as a doctor has ended (step S1I).

If the operation detection unit 942 does not detect that the pressing of the switch 541 has ended (step S1I: No), the control device 9 returns to step S1D.

On the other hand, when the operation detection unit 942 detects that the pressing of the switch 541 has ended (step S1I: Yes), the determination unit 943 ends the measurement of the pressing time (step S1J). Then, the control device 9 proceeds to step S1K.

Figure 6:
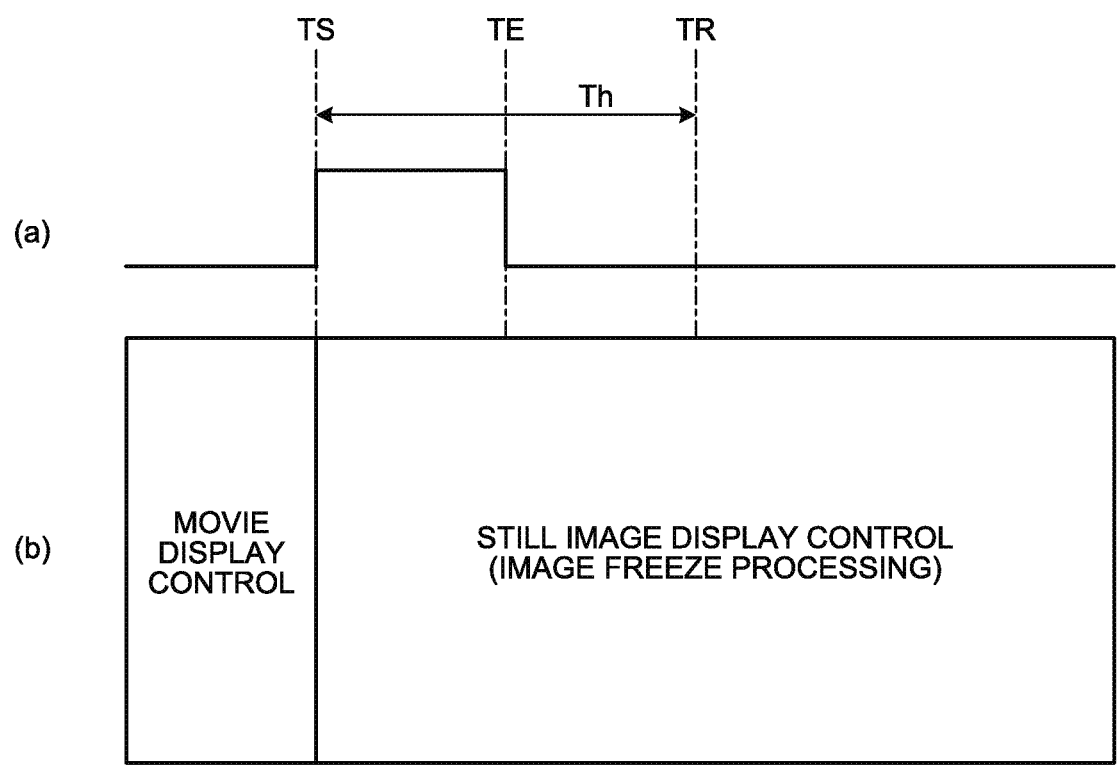
FIG. 6 is a time chart illustrating an operation of the control device.

FIG. 6 is a time chart illustrating control performed by the display controller 941 in steps S1A to S1D, S1I, and S1J described above when the switch 541 is short pressed by the user such as a doctor (when pressing of the switch 541 ends before the predetermined time Th is exceeded).

The steps S1A to S1D, S1I, and S1J described above are summarized as follows.

As illustrated in FIG. 6, when the operation detection unit 942 detects that the switch 541 has been pressed while the movie display control is being executed (step S1A: Yes), the display controller 941 switches from the movie display control to the still image display control at the pressing start timing TS (step S1B). Then, when the pressing of the switch 541 ends before the pressing time reaches the predetermined time Th (Step S1I: Yes), the display controller 941 continues the still image display control without performing the image release processing (Step S1F).

After step S1J, the operation detection unit 942 constantly monitors whether or not the switch 541 is pressed by a user such as a doctor while the still image display control is being performed (step S1K).

When the operation detection unit 942 detects the pressing of the switch 541 (step S1K: Yes), the determination unit 943 starts measuring the pressing time during which the switch 541 is continuously pressed (step S1L).

After step S1L, the determination unit 943 determines whether or not the measured pressing time has reached a predetermined time Th (step S1M).

When it is determined that the pressing time has reached the predetermined time Th (step S1M: Yes), the determination unit 943 ends the measurement of the pressing time (step S1N). Furthermore, the display controller 941 executes the image release processing as in step S1F (step S1O).

In FIG. 4, for the sake of description, step S1O is executed after step S1N. Actually, however, steps S1N and S1O are executed substantially simultaneously.

After step S1O, the display controller 941 switches from the still image display control to the movie display control as in step S1G (step S1P).

After step S1P, the operation detection unit 942 constantly monitors whether the pressing of the switch 541 by the user such as a doctor has ended (step S1Q).

If the operation detection unit 942 detects that the pressing of the switch 541 has ended (step S1Q: Yes), the control device 9 returns to step S1A.

Figure 7:
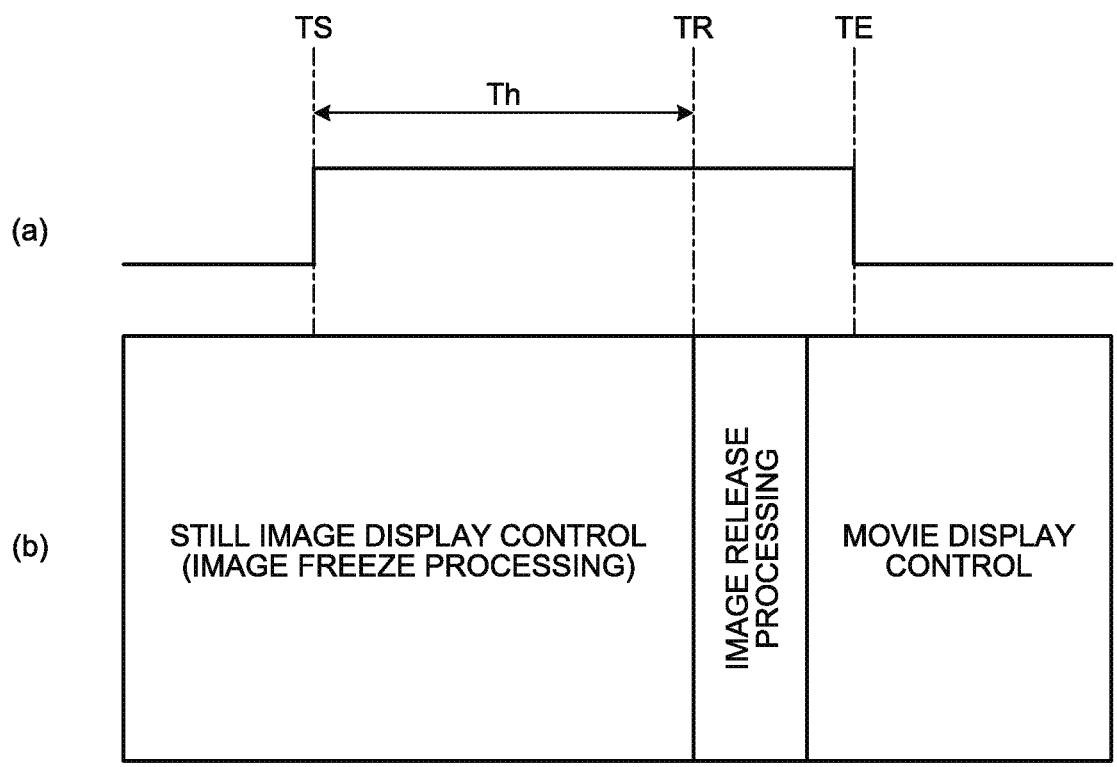
FIG. 7 is a time chart illustrating an operation of the control device.

FIG. 7 is a time chart illustrating the control performed by the display controller 941 in steps S1K to S1Q described above when the switch 541 is long pressed by the user such as a doctor.

Steps S1K to S1Q described above are summarized as follows.

As illustrated in FIG. 7, when the operation detection unit 942 detects the pressing of the switch 541 while the still image display control is being executed (step S1K: Yes) and when the determination unit 943 determines that the pressing time has reached the predetermined time Th (step S1M: Yes), the display controller 941 executes the image release processing at the reaching timing TR (FIG. 7) at which the predetermined time Th is reached (step S1O). The timing for executing the image release processing may be the pressing end timing TE as long as it is after the reaching timing TR.

Then, the display controller 941 switches from the still image display control to the movie display control (step S1P).

Returning to step S1M, when it is determined that the pressing time has not reached the predetermined time Th (step S1M: No), the operation detection unit 942 determines whether the pressing of the switch 541 by the user such as a doctor has ended (step S1R).

When the operation detection unit 942 does not detect that the pressing of the switch 541 has ended (step S1R: No), the control device 9 returns to step S1M.

On the other hand, when the operation detection unit 942 detects that the pressing of the switch 541 has ended (step S1R: Yes), the determination unit 943 ends the measurement of the pressing time (step S1S). The display controller 941 switches from the still image display control to the movie display control as in step S1G (step S1T). Thereafter, the control device 9 returns to step S1A.

In FIG. 4, for the sake of description, step S1T is executed after step S1S. Actually, however, steps S1S and S1T are executed substantially simultaneously.

Figure 8:
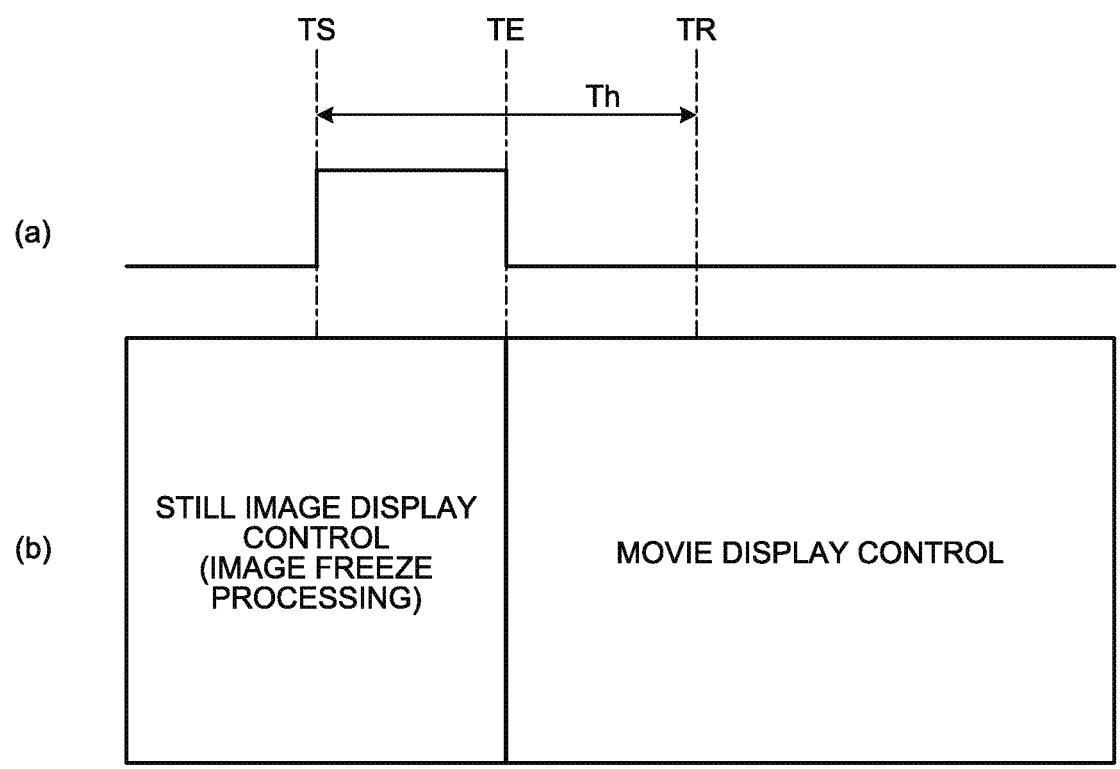
FIG. 8 is a time chart illustrating an operation of the control device.

FIG. 8 is a time chart illustrating the control performed by the display controller 941 in steps S1K to S1M and S1R to S1T described above when the switch 541 is short pressed by the user such as a doctor.

Steps S1K to S1M and S1R to S1T described above are summarized as follows.

As illustrated in FIG. 8, when the operation detection unit 942 detects the pressing of the switch 541 while the still image display control is being executed (step S1K: Yes) and when the pressing of the switch 541 ends before the pressing time reaches the predetermined time Th (step S1R: Yes), the display controller 941 switches from the still image display control to the movie display control at the pressing end timing TE (step S1T).

The first embodiment described above provides the following effect.

In the observation system 1 according to the first embodiment, when the operation detection unit 942 detects that the switch 541 is pressed while the movie display control is being executed, the display controller 941 switches from the movie display control to the still image display control at the pressing start timing TS. As a result, the image displayed at the pressing start timing TS is displayed on the display device 7 as a still image. Then, when the determination unit 943 determines that the pressing time has reached the predetermined time Th, the display controller 941 executes the image release processing at the reaching timing TR at which the predetermined time Th is reached.

Thus, the image displayed at the pressing start timing TS is displayed as a still image on the display device 7, so that the user may check the images, and may long press the switch 541 when a desired image is displayed to store the image in the storage unit 97 as a still image. On the other hand, if the user checking the image determines that the image is not a desired image, the user may avoid storing the image in the storage unit 97 by short pressing the switch 541.

Thus, the observation system 1 according to the first embodiment enables an image desired by a user to be stored as a still image to improve usability.

In the observation system 1 according to the first embodiment, when the operation detection unit 942 detects that the switch 541 has been pressed while the movie display control is being executed, the display controller 941 switches from the movie display control to the still image display control at the pressing start timing TS. The display controller 941 continues the still image display control when the pressing of the switch 541 ends before the pressing time reaches the predetermined time Th. When the operation detection unit 942 detects the pressing of the switch 541 while the still image display control is being executed and when the determination unit 943 determines that the pressing time has reached the predetermined time Th, the display controller 941 executes the image release processing at a reaching timing TR at which the predetermined time Th is reached.

Specifically, the short pressing results in the still image display control being continued. Thus, the user short presses the switch 541 when he or she wants to check the image stored in the storage unit 97 for a sufficiently long period of time. Then, the user checks the image, and if it is a desired image, the user may store the image as a still image in the storage unit 97 by long pressing the switch 541 again. Thus, usability may further be improved.

In the observation system 1 according to the first embodiment, when the operation detection unit 942 detects that the switch 541 has been pressed while the movie display control is being executed, the display controller 941 switches from the movie display control to the still image display control at the pressing start timing TS. The display controller 941 continues the still image display control when the pressing of the switch 541 ends before the pressing time reaches the predetermined time Th. Furthermore, when the operation detection unit 942 detects the pressing of the switch 541 while the still image display control is being executed and when the pressing of the switch 541 ends before the pressing time reaches the predetermined time Th, the display controller 941 switches from the still image display control to the movie display control.

Specifically, the short pressing results in the still image display control being continued. Thus, the user short presses the switch 541 when he or she wants to check the image stored in the storage unit 97 for a sufficiently long period of time. Then, the user checks the image, and if it is not a desired image, the user may short press the switch 541 again to return to the movie display. Thus, usability may further be improved.

Second Embodiment

Next, a second embodiment will be described.

In the following description, the same reference numerals are given to components that are the same as those in the first embodiment described above, and detailed description thereof will be omitted or simplified.

Figure 9:
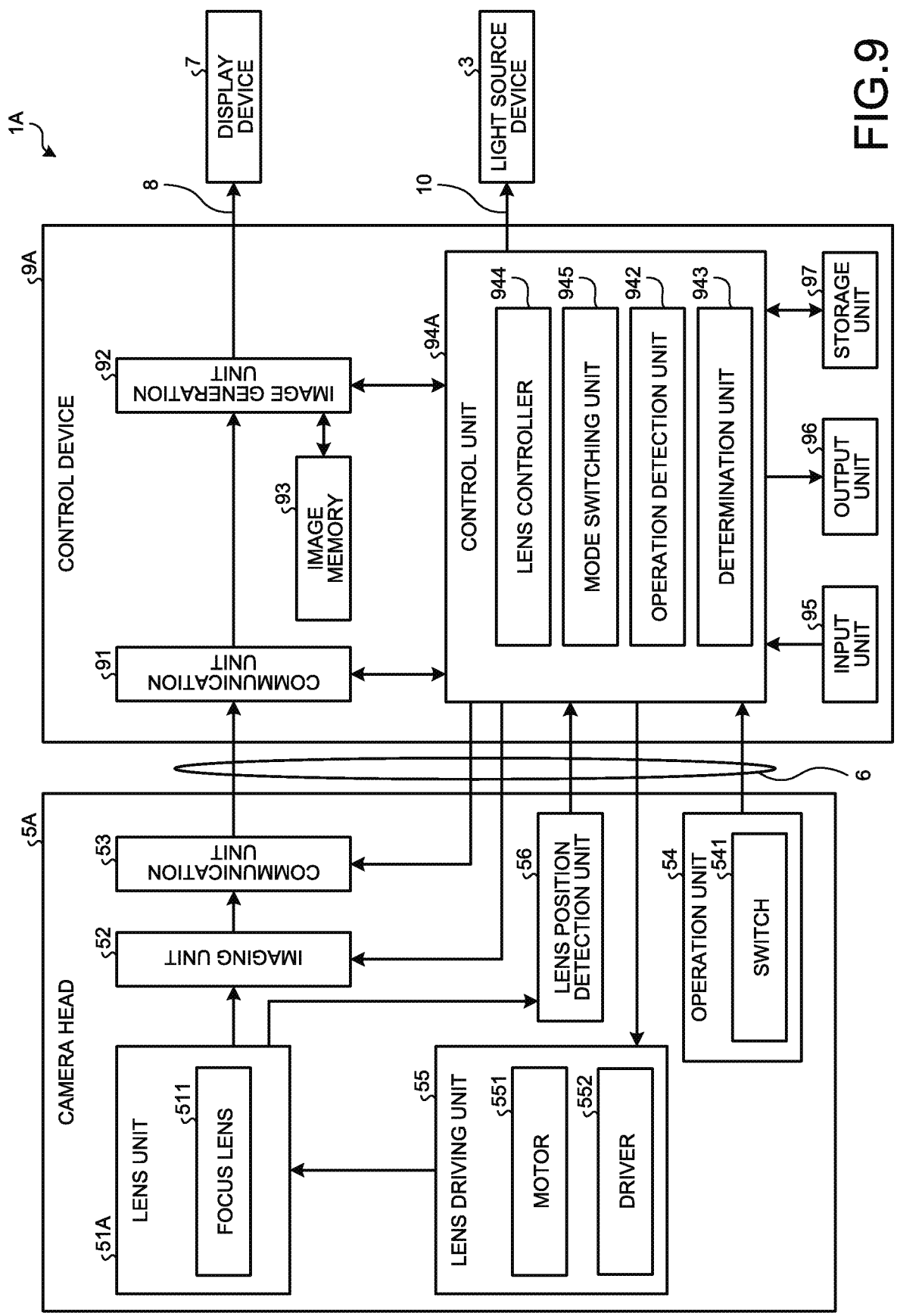
FIG. 9 is a diagram illustrating a configuration of an observation system according to a second embodiment.

FIG. 9 is a diagram illustrating a configuration of an observation system 1A according to the second embodiment. Specifically, FIG. 9 is a block diagram corresponding to FIG. 2.

The observation system 1A according to the second embodiment is different from the observation system 1 described above in the first embodiment in the functions executed by the long pressing and short pressing of the switch 541. Hereinafter, configurations of a camera head 5A and a control device 9A in the observation system 1A will be described in order.

Configuration of Camera Head

The camera head 5A corresponds to the imaging capturing device. As illustrated in FIG. 9, this camera head 5A is different from the camera head 5 described above in the first embodiment in that a lens unit 51A having a configuration different from the lens unit 51 is employed, and that a lens driving unit 55 and a lens position detection unit 56 are added.

As illustrated in FIG. 9, the lens unit 51A is formed by one or a plurality of lenses, and includes a focus lens 511 that moves along an optical axis for focus adjustment. The lens unit 51A is provided with a focus mechanism (not illustrated) that moves the focus lens 511 along the optical axis.

As illustrated in FIG. 9, the lens driving unit 55 includes a motor 551 that operates the focus mechanism described above, and a driver 552 that drives the motor 551. The lens driving unit 55 performs the focus adjustment for the lens unit 51A under the control of the control device 9A.

The lens position detection unit 56 is formed by using a position sensor such as a photo interrupter, and detects the lens position of the focus lens 511 (hereinafter referred to as a focus position). Then, the lens position detection unit 56 outputs a detection signal corresponding to the focus position to the control device 9A through the first transmission cable 6.

Configuration of Control Device

As illustrated in FIG. 9, the control device 9A is different from the control device 9 described in the first embodiment in that a control unit 94A having a function different from that of the control unit 94 is employed.

Here, the image generation unit 92 according to the second embodiment generates only the first video signal of the first and second video signals described in the first embodiment. The image generation unit 92 executes detection processing described below for controlling the camera head 5A (execution of autofocus control (hereinafter referred to as AF processing)) on the image signal read from the image memory 93.

For example, based on pixel information (such as a luminance signal (Y signal) for example) about each pixel in a detection region which is a partial region in the entire captured image for a single frame captured by the imaging unit 52, the image generation unit 92 detects contrast and a frequency component of an image in the detection region. Then, the image generation unit 92 outputs detection information (such as contrast and frequency component) obtained by the detection to the control unit 94A.

As illustrated in FIG. 9, the control unit 94A is different from the control unit 94 described above in the first embodiment in that the functions of the display controller 941 are omitted, and in that the functions of a lens controller 944 and a mode switching unit 945 are added.

The lens controller 944 executes the AF processing for focus adjustment for the lens unit 51A as described below.

Specifically, the lens controller 944 sequentially calculates a focus evaluation value while operating the lens driving unit 55 and moving the focus lens 511 along the optical axis. Furthermore, the lens controller 944 causes the storage unit 97 to sequentially store focus information in which the focus position detected by the lens position detection unit 56 is associated with the focus evaluation value corresponding to this focus position.

Here, as the focus evaluation value, the contrast (detection information) detected by the image generation unit 92 and the sum of high-frequency components among the frequency components (detection information) detected by the image generation unit 92 are usable for example. A larger focus evaluation value indicates that the subject is more in focus.

The lens controller 944 calculates a peak position (focus position) at which the largest focus evaluation value is obtained, based on a plurality of pieces of focus information stored in the storage unit 97. The lens controller 944 calculates a movement direction (direction toward the near point or toward the far point) and a movement amount for moving the focus lens 511 to the peak position, based on the peak position and the current focus position detected by the lens position detection unit 56. Then, the lens controller 944 outputs a control signal corresponding to the movement direction and the movement amount to the lens driving unit 55, to position the focus lens 511 at the peak position.

As described above, in the second embodiment, the lens controller 944 executes the AF processing by so-called hill climbing.

The mode switching unit 945 switches between a first autofocus mode (hereinafter, referred to as a first AF mode) for allowing the lens controller 944 to execute the AF processing only once and a second autofocus mode (hereinafter, referred to as a second AF mode) for causing the lens controller 944 to continuously execute the AF processing.

The first AF mode is so-called one-touch AF. The second AF mode is so-called continuous AF.

Operation of Control Device

Figure 10:
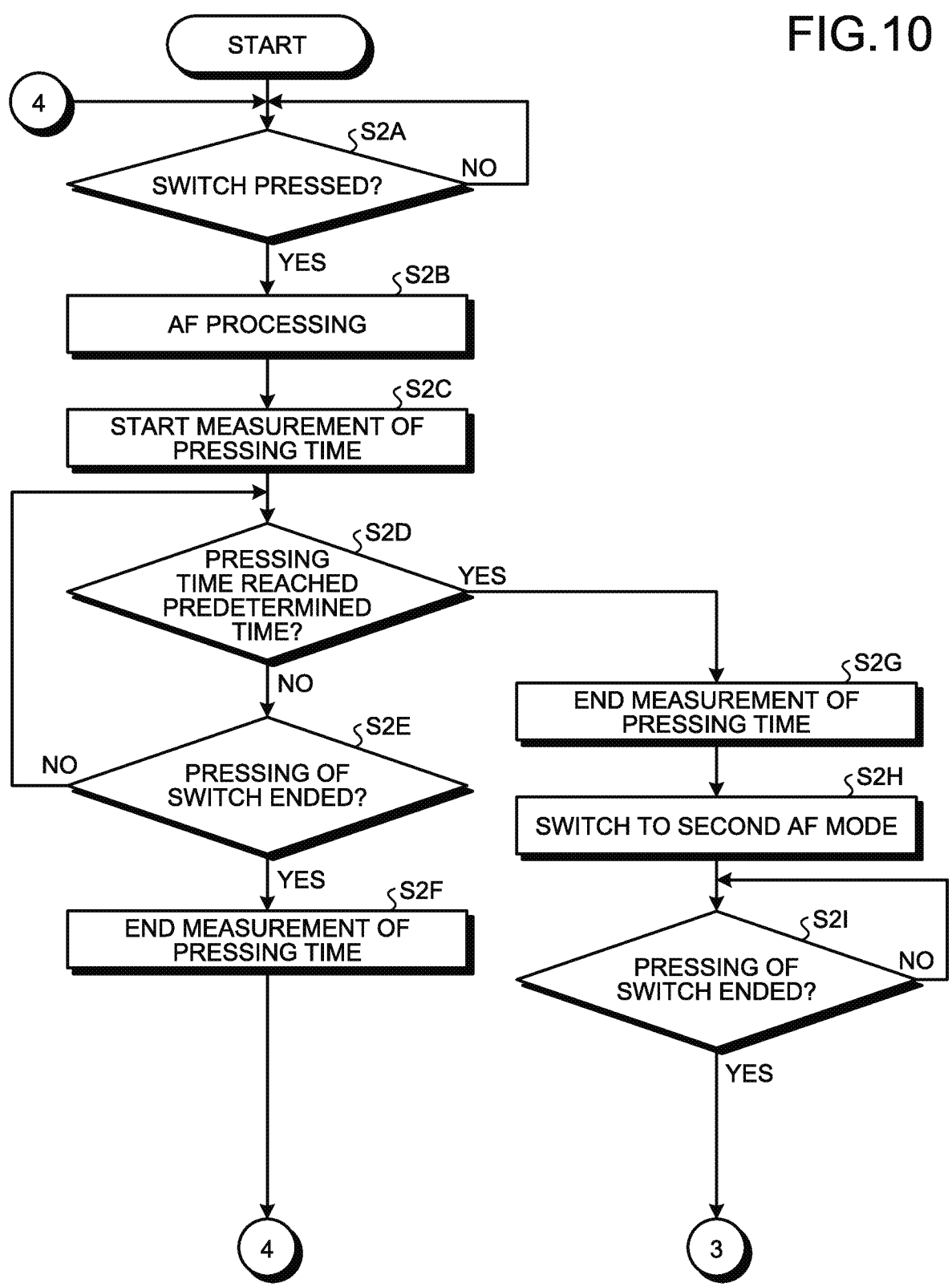
FIG. 10 is a flowchart illustrating an operation of the control device.
Figure 11:
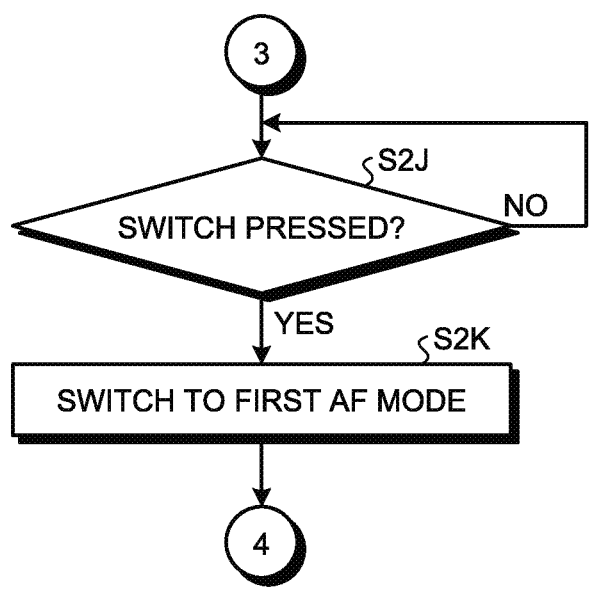
FIG. 11 is a flowchart illustrating an operation of the control device.
Figure 12:
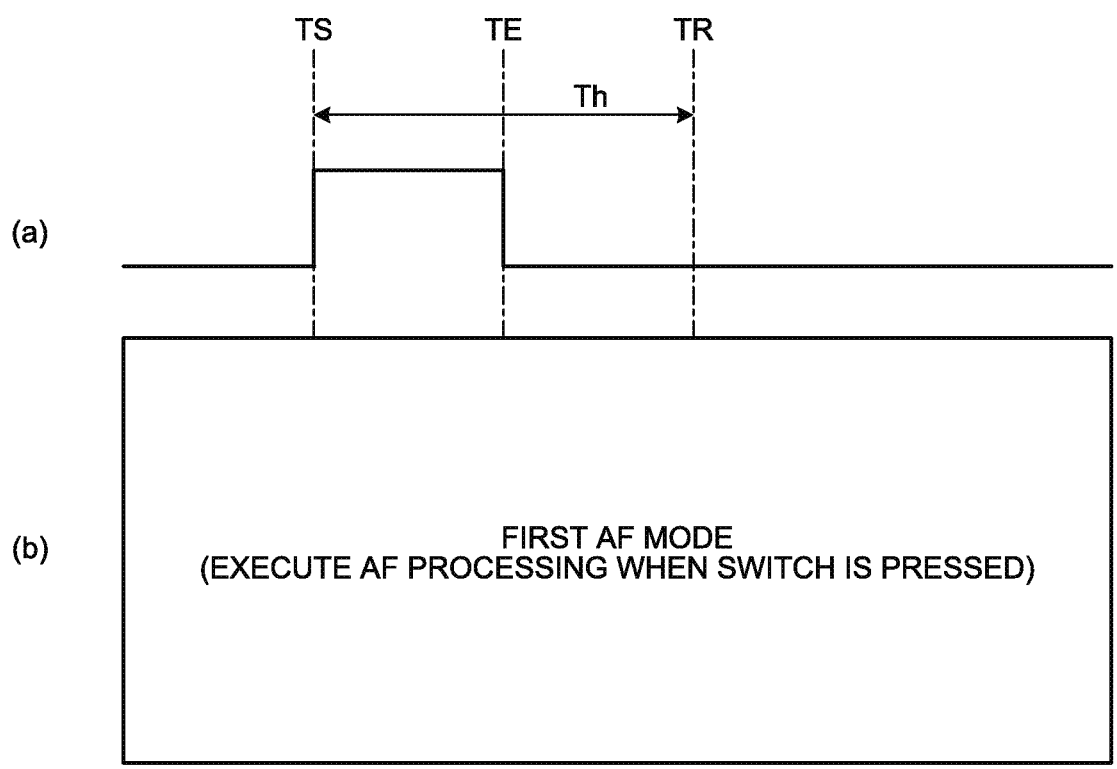
FIG. 12 is a time chart illustrating an operation of the control device.
Figure 13:
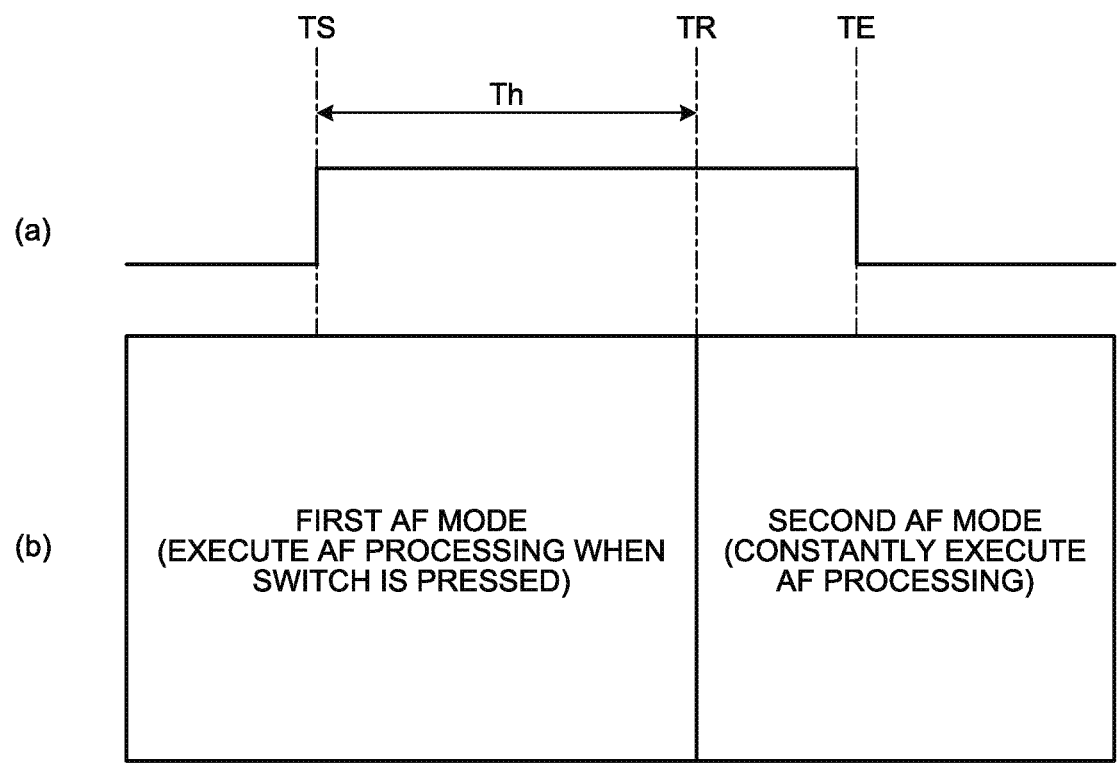
FIG. 13 is a time chart illustrating an operation of the control device.

FIGS. 10 and 11 are flowcharts illustrating operations of the control device 9A. FIGS. 12 and 13 are time charts illustrating operations of the control device 9A. Specifically, (a) in FIGS. 12 and 13 illustrate an operation signal output from the switch 541, as in (a) in FIGS. 5 to 8. Furthermore, (b) in FIGS. 12 and 13 illustrate the AF mode set by the mode switching unit 945.

Next, the operations of the control device 9A described above will be described with reference to FIGS. 10 to 13. Hereinafter, for the sake of description, the control device 9A is assumed to execute the following steps S2A to S2K in the state of the first AF mode.

First of all, the operation detection unit 942 constantly monitors whether the switch 541 has been pressed by a user such as a doctor (step S2A).

When the operation detection unit 942 detects that the pressing of the switch 541 has ended (step S2A: Yes), the lens controller 944 executes the AF processing (step S2B). Furthermore, the determination unit 943 starts measuring the pressing time during which the switch 541 is continuously pressed (step S2C).

In FIG. 10, for the sake of description, step S2C is executed after step S2B. Actually, however, steps S2B and S2C are executed substantially simultaneously.

After step S2C, the determination unit 943 determines whether the measured pressing time has reached a predetermined time Th (FIGS. 12 and 13) (step S2D).

When it is determined that the pressing time has not reached the predetermined time Th (step S2D: No), the operation detection unit 942 determines whether the pressing of the switch 541 by the user such as a doctor has ended (step S2E).

When the operation detection unit 942 does not detect that the pressing of the switch 541 has ended (step S2E: No), the control device 9A returns to step S2D.

On the other hand, when the operation detection unit 942 detects that the pressing of the switch 541 has ended (step S2E: Yes), the determination unit 943 ends the measurement of the pressing time (step S2F). Thereafter, the control device 9A returns to step S2A.

FIG. 12 is a time chart illustrating the AF mode set by the mode switching unit 945 in steps S2A to S2F described above when the switch 541 is short pressed by the user such as a doctor.

Steps S2A to S2F described above are summarized as follows.

When the operation detection unit 942 detects the pressing of the switch 541 under the first AF mode (step S2A: Yes), the mode switching unit 945 causes the lens controller 944 to execute the AF processing only once at the pressing start timing TS (step S2B). Then, when the pressing of the switch 541 ends before the pressing time reaches the predetermined time Th (step S2E: Yes), the mode switching unit 945 does not switch to the second AF mode and continues the first AF mode.

Returning to step S2D, when it is determined that the pressing time has reached the predetermined time Th (step S2D: Yes), the determination unit 943 ends the measurement of the pressing time (step S2G). Furthermore, the mode switching unit 945 switches the first AF mode to the second AF mode (step S2H).

In FIG. 10, for the sake of description, step S2H is executed after step S2G. Actually, however, steps S2H and S2G are executed substantially simultaneously.

After step S2H, the operation detection unit 942 constantly monitors whether the pressing of the switch 541 by the user such as a doctor has ended (step S2I).

When the operation detection unit 942 detects that the pressing of the switch 541 has ended (step S2I: Yes), the control device 9A proceeds to step S2J.

FIG. 13 is a time chart illustrating the AF mode set by the mode switching unit 945 in steps S2A to S2D and S2G to S2I described above when the switch 541 is long pressed by the user such as a doctor.

The steps S2A to S2D and S2G to S2I described above are summarized as follows.

When the operation detection unit 942 detects the pressing of the switch 541 under the first AF mode (step S2A: Yes), the mode switching unit 945 causes the lens controller 944 to execute the AF processing only once at the pressing start timing TS (step S2B). Then, when the determination unit 943 determines that the pressing time has reached the predetermined time Th (Step S2D: Yes), the mode switching unit 945 switches the first AF mode to the second AF mode at the reaching timing TR (FIG. 13) at which the predetermined time Th is reached (step S2H). As a result, the lens controller 944 constantly executes the AF processing. The timing for switching to the second AF mode may be the pressing end timing TE as long as it is after the reaching timing TR.

After step S2I, the operation detection unit 942 constantly monitors whether or not the switch 541 has been pressed by a user such as a doctor in the second AF mode (step S2J).

When the operation detection unit 942 detects the pressing of the switch 541 (step S2J: Yes), the mode switching unit 945 switches from the second AF mode to the first AF mode (step S2K). Thereafter, the control device 9A returns to step S2A.

The second embodiment described above provides the following effect.

In the observation system 1A according to the second embodiment, switching between the first and second AF modes may be implemented by long pressing or short pressing the switch 541. Thus, two functions may be executed using one switch 541, whereby usability may be improved.

OTHER EMBODIMENTS

The embodiments for carrying out the present disclosure have been described above, but the present disclosure should not be limited only by the above-described first and second embodiments.

In the first and second embodiments described above, the short pressing and long pressing of the switch 541 are employed as a first operation, but this should not be construed in a limiting sense.

For example, the switch 541 is formed by a push button switch that may be operated in two stages of half pressing and full pressing. The half pressing of the push button switch may be the first operation, and the full pressing of the push button switch may be a second operation.

For example, a single clicking of the switch 541 may be the first operation, and a double clicking of the switch 541 may be the second operation.

In the first and second embodiments described above, a part of the configuration of the camera heads 5 and 5A and a part of the configuration of the control devices 9 and 9A may be provided in, for example, the connector CN1 or the connector CN2.

In the first and embodiments described above, the control device is installed in the observation systems 1 and 1A in which the insertion portion 2 is formed by a rigid endoscope. However, this should not be construed in a limiting sense. For example, the control device may be installed in an observation system in which the insertion portion 2 is formed by a flexible endoscope. Furthermore, the control device may be installed in an observation system such as a surgical endoscope (see, for example, Japanese Patent Application Laid-Open No. 2016-42981) for observing a certain field of view area inside a subject (inside a living body) or a surface of the subject (living body surface) with the area enlarged.

The observation systems 1 and 1A according to the first and second embodiments described above are not limited to the medical field, and may also be a system used in an industrial field for observing the inside of a subject such as a mechanical structure.

With the control device and the observation system, usability may be improved.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A control device comprising:
   a processor comprising hardware, the processor being configured to:
      perform movie display control of causing a display to sequentially display a plurality of images acquired in time series, and still image display control of causing the display to display any of the plurality of images as a still image;
      detect a first operation on a switch by a user;
      switch, when the first operation is detected while the movie display control is being executed, from the movie display control to the still image display control and causing the display to display, as a still image, an image displayed at a timing at which the first operation is detected;
      cause, when the processor determines that a continued time period during which the processor detects the first operation reaches a predetermined time period, a memory to store the image displayed as a still image under the still image display control; and
      switch from the still image display control to the movie display control after the image displayed as a still image is stored in the memory regardless of whether the user continues the first operation.

2. The control device according to claim 1, wherein
the switch is formed by a push button switch, and
the processor is configured to detect pressing of the switch by the user as the first operation.

3. The control device according to claim 1, wherein
the switch is formed by a button switch operable in two stages that are half pressing and full pressing,
the processor is configured to detect the half pressing of the switch by the user as the first operation and detect the full pressing of the switch by the user as a second operation, and
the processor is configured to determine that the predetermined operation condition is satisfied when the processor detects the first operation and then detects the second operation.

4. The control device according to claim 1, wherein the processor is configured to:
switch from the movie display control to the still image display control when the processor detects the first operation while the movie display control is being executed, and cause the display to display, as a still image, an image displayed at a timing when the first operation is detected, and
continue the still image display control when the processor determines that the predetermined operation condition is not satisfied.

5. The control device according to claim 4, wherein the processor is configured to cause the memory to store the image displayed as a still image under the still image display control when the processor detects the first operation while the still image display control is being executed and when the processor determines that the predetermined operation condition is satisfied.

6. The control device according to claim 4, wherein
the processor is configured to switch from the still image display control to the movie display control when the processor detects the first operation while the still image display control is being executed and when the processor determines that the predetermined operation condition is not satisfied.

7. An observation system comprising
the control device according to claim 1.

8. A control method comprising:
performing movie display control of causing a display to sequentially display a plurality of images acquired in time series, and still image display control of causing the display to display any of the plurality of images as a still image;
detecting a first operation on a switch by a user;
measuring, by a processor, a time period during which the first operation is continuously carried out;
switching, when the first operation is detected while the movie display control is being executed, from the movie display control to the still image display control and causing the display to display, as a still image, an image displayed at a timing at which the first operation is detected;
storing the image displayed as a still image under the still image display control in response to the time period reaching a predetermined time period; and
switching from the still image display control to the movie display control after the image displayed as a still image is stored regardless of whether the user continues the first operation.

\* \* \* \* \*